United States Patent [19]

Nekovar

[11] Patent Number: 4,955,043
[45] Date of Patent: Sep. 4, 1990

[54] X-RAY DIAGNOSTICS INSTALLATION

[75] Inventor: Anton Nekovar, Erlangen, Fed. Rep. of Germany

[73] Assignee: Siemens Aktiengesellschaft, Berlin and Munich, Fed. Rep. of Germany

[21] Appl. No.: 244,153

[22] Filed: Sep. 14, 1988

[30] Foreign Application Priority Data

Sep. 28, 1987 [DE] Fed. Rep. of Germany ....... 3732634

[51] Int. Cl.$^5$ .............................................. H05G 1/44
[52] U.S. Cl. ....................................... 378/108; 378/99; 378/95
[58] Field of Search ............................... 378/108–112, 378/99, 117, 95; 358/111

[56] References Cited

U.S. PATENT DOCUMENTS

| | | | |
|---|---|---|---|
| 4,473,843 | 9/1984 | Bishop et al. | 358/111 |
| 4,517,594 | 5/1985 | Horbaschek | 358/111 |
| 4,747,118 | 5/1988 | Spaak | 378/108 |
| 4,748,511 | 5/1988 | Nichols et al. | 358/111 |
| 4,809,309 | 2/1989 | Beekmans | 358/111 |

FOREIGN PATENT DOCUMENTS 0097355 1/1984 European Pat. Off. .
0149103 7/1985 European Pat. Off. .
OS3600464 7/1987 Fed. Rep. of Germany .
60-22634 2/1985 Japan .

OTHER PUBLICATIONS

"Imaging Systems for Digital Radiography: Present Status and Future Prospects," Schittenhelm, Electromedica 54, No. 2, pp. 72–81 (1986).

Primary Examiner—Craig E. Church
Assistant Examiner—John C. Freeman
Attorney, Agent, or Firm—Hill, Van Santen, Steadman & Simpson

[57] ABSTRACT

An x-ray diagnostics installation has an x-ray source, an x-ray image intensifier connected to a video chain and a processing circuit which controls various components of the installation. The processing circuit includes a weighting circuit which allocates an individual weighting factor to different regions of the x-ray image. The processing circuit also includes an evaluation circuit, connected to the weighting circuit, which combines the signals from the weighted image regions to form an actual value signal, which is used to control certain of the components of the installation.

6 Claims, 2 Drawing Sheets

X-RAY DIAGNOSTICS INSTALLATION

BACKGROUND OF THE INVENTION

1. Field of the Invention

The present invention is directed to an x-ray diagnostics installation, and in particular to such a diagnostics installation having an x-ray source, an x-ray image intensifier connected to a video chain, a processing circuit which controls certain of the installation components, and a monitor on which the image is displayed.

2. Description of the Prior Art

German No. OS 32 25 061, corresponding to U.S. Pat. No. 4,517,594, discloses an x-ray diagnostics installation wherein a portion of the output image from the x-ray image intensifer is coupled by a light distributor onto a detector, which consists of a matrix of photosensors. The parallel outputs of the photosensors are connected to a summing amplifier is respective switches. The output signals from the individual photosensors are weighted by variable resistors.

A disadvantage of this installation is that a light distributor must be provided. Additionally, the structure of the matrix is relatively complicated, because each photosensor must have an amplifier connected thereto. Because the amplifiers occupy a portion of the total matrix area, space limitations impose a limit on the number of photosensors per unit area which can be used. Additionally, even though the weighting resistors can be varied, the resistors retain the set value until re-set, and thus it is not possible to undertake a continuous or dynamic modification and matching of the weighting.

SUMMARY OF THE INVENTION

It is an object of the present invention to provide an x-ray diagnostics installation wherein the x-ray image can be more finely, and thus more precisely, subdivided than in conventional systems.

Another object of the present invention is to provide such an x-ray diagnostics installation wherein continuous modification of the weighting of the various image portions can be achieved without substantial additional outlay for expensive components.

The above objects are achieved in accordance with the principles of the present invention in an x-ray diagnostics installation having a processing circuit which includes a weighting circuit that allocates a respective individual weighting factor to different image areas of the total image. The weighting circuit is connected to an evaluation circuit, also in the processing circuit, which combines the measured signals from the weighted image regions to form an actual value signal. In this installation, it is possible to re-calculate the individual weighting factors for each image region, and to undertake corrections, as needed, during the acquisition of the actual value signal.

A rapid digital processing consisting of simple circuits can be achieved in a further embodiment of the invention having a circuit for data reduction of the video signal from the video camera. In this circuit, a plurality of picture elements are combined into the image regions, the reduction circuit proceeding the weighting circuit. The image regions are then weighted in the weighting circuit.

X-ray installations having so-called organ programming are known in the art. The conventional organ programming circuit can be connected to the weighting circuit to control the weighting factors based on the organ which is being examined.

In another embodiment of the invention, a circuit for generating histograms is connected to the weighting circuit, and controls the selection of the weighting factors. Stored values can be accessed by connecting the circuit for generating histograms to a detector circuit for pattern recognition.

The processing circuit can be connected to the x-ray generator for controlling the dose power based on the actual value signal, and may also be connected to an adjustment circuit which controls the size of the central opening in an iris diaphragm, also based on the actual value signal. The video camera may contain a controlled-gain video amplifier, which may also be connected to the processing circuit, with the gain being controlled by the actual value signal.

DESCRIPTION OF THE PREFERRED EMBODIMENTS

Figure 1:
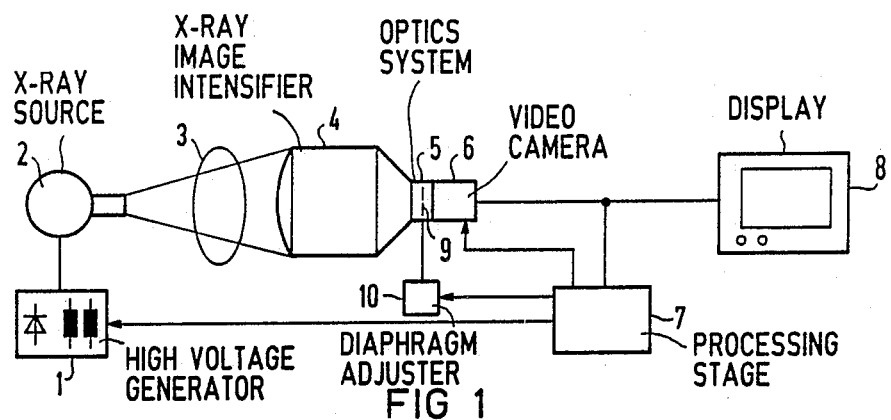
FIG. 1 is a block circuit diagram of an x-ray diagnostics installation constructed in accordance with the principles of the present invention.

As shown in FIG. 1, an x-ray diagnostics installation has an x-ray source 2 driven by a high voltage generator 1, which emits an x-ray beam that penetrates a patient 3. The x-ray beam, attenuated by the patient 3, is incident on the input luminescent screen of an x-ray image intensifier 4, which converts the radiation image into a visible image. A video chain including a video camera 6 is coupled to the output screen of the x-ray image intensifier 4 via an optics system 5. The video camera 6 converts the output image of the x-ray image intensifier into an electrical BA signal, which is supplied to a processing circuit 7, and to a monitor 8 which visually displays the radiation image. The processing circuit 7 is connected to the high voltage generator 1 for control thereof, and is also connected to an adjustment circuit 10 for an iris diaphragm 9 in the optics system 5. In addition to the iris diaphragm 9, or in place thereof, the video camera 6 may contain a controlled-gain video amplifier, and the processing circuit 7 may be connected to the control input of this amplifier.

Figure 2:
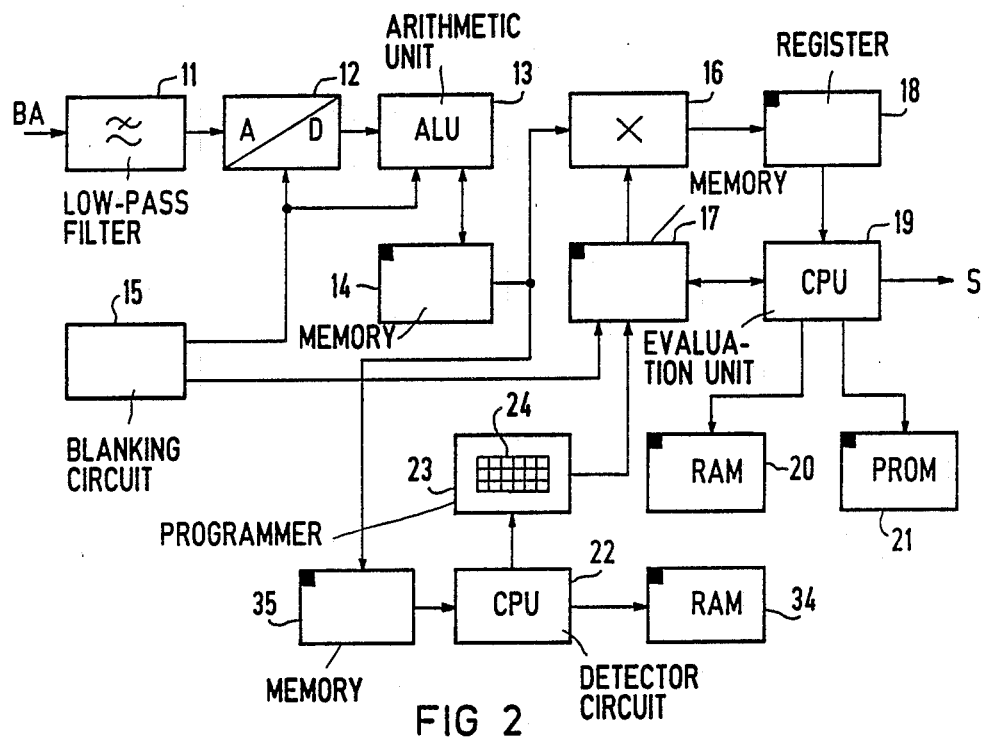
FIG. 2 is a block diagram of a digital embodiment of a processing circuit constructed in accordance with the principles of the present invention for the installation of FIG. 1.

A digital embodiment of the processing circuit 7 is shown in FIG. 2. The BA signal from the video camera 6 is supplied to a low-pass filter 11, having an output connected to an analog-to-digital converter 12. The digital output signal of the converter 12 is supplied to an arithmetic unit 13, which is connected to a memory 14. A multiplier 16, in which the output signal from the memory 14 is multiplied by values supplied by a coefficient memory 17, is connected to the output of the memory 14. The output values multiplied by these different coefficients are intermediately stored in a register memory 18. An evaluation circuit 19, for example, a microprocessor (CPU), is connected to the register memory 18, and forms a histogram, i.e., the brightness distribution of the image, from the stored values. The histograms formed by the register memory 18 are stored in a memory 20, for example, a RAM. A program memory 21, for example, a PROM, is also connected to the evaluation circuit 19.

A blank circuit 15 is connected to the converter 12, the arithmetic unit 13, and the coefficient memory 17. The blanking circuit 15 controls those components. A detector circuit 22, for example, a microprocessor (CPU) is connected to the memory 13 via an intermediate memory 35 and the memory 14. A memory 34, in which an unweighted histogram calculated by the detector circuit 22 is stored, is connected to the detector 22. The detector circuit 22 is also connected to a programmer 23, such as an organ programmer as is known in the art, which includes a keyboard 24 by which operating values programmed for examination of a specific organ can be selected in a known manner. These values are supplied to the coefficient memory 17, wherein the coefficients are varied in accordance with the selected organ, so that a weighting of the measured values dependent on the selected organ ensues.

The arithmetic unit 13 and the memory 14 constitute a circuit for data reduction of the video signal from the video camera 6. These components, in combination, combine a plurality of picture elements from the video camera 6 to form an image region, so that a reduced matrix of measured values is obtained. This matrix is preferably a 32×32 matrix. This means that the digital image which, for example, contains 512×512 picture elements, is combined to form a new matrix of image regions each having an area of 256 picture elements. The operating speed of currently available central processing units (microprocessors) is thus sufficient for further processing of the data. The values of the matrix are then multiplied by the coefficients from the cofficient memory 17. Each field of the matrix, i.e., each image area, is given an arbitrary weighting factor which may assume, for example, values from 0 through 1. Differing measuring zones in which the image is differently weighted can thus be obtained. The weighted measured values are stored in the register memory 18, from which they are called by the evaluation circuit 19. A histogram is then calculated from these measured values, and is stored in the memory 20. The evaluation circuit 19 calculated an actual value S for the brightness from these stored values, and controls the dose power of the high voltage generator 1 on the basis of this signal. The actual value signal can also be supplied to the diaphragm adjustor 10, to control the size of the opening of the iris diaphragm 9. If the video camera 6 has a controlled-gain video amplifier, the actual value signal can additionally, or alternatively, be supplied to the gain input of this amplifier for control thereof.

Using the unweighted histogram stored in the memory 35, the detector 22 undertakes a pattern recognition, and controls the programmer 23. The detector circuit 22 identifies regions, for example, laterally from the extremities, cause an overdose of radiation in the image, and thus should not contribute to the weighting. Under the control of the programmer 23, corrected in accordance with the aforementioned pattern recognition, the coefficients in the coefficient memory 17 are also varied, so that the weighting of the subsequent images is undertaken on the basis of these measured values.

The blanking circuit 15 undertakes circuit blanking, i.e., the blanking of the video signal which is not a part of the radiation image. It also sets the corresponding values to zero so that they do not contribute to the calculation of the measured image.

Figure 3:
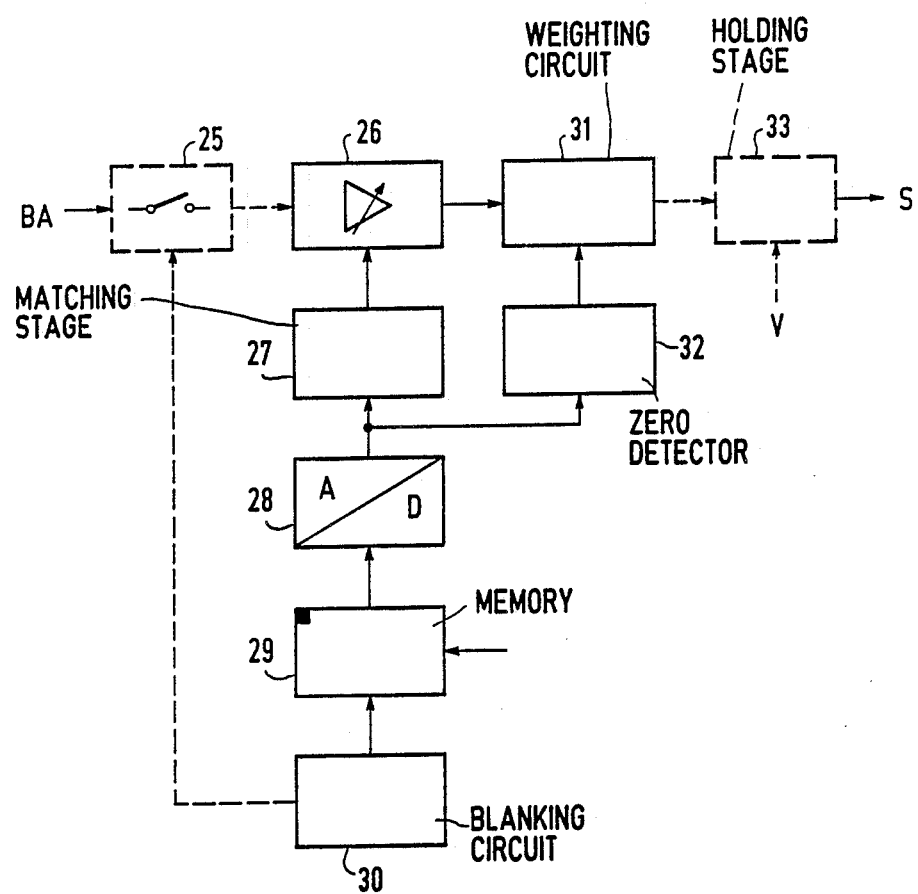
FIG. 3 is a block diagram of an analog version of a portion of the processing circuit of FIG. 1.

An analog embodiment of the processing circuit 7 is shown in FIG. 3. In this embodiment, the BA signal from the video camera 6 is supplied to a video switch 25, which is connected to a controllable amplifier 26. The controllable amplifier 26 is supplied with gain factors from a coefficient memory 29 via a digital-to-analog converter 28 and a matching stage 27. A blanking circuit 30, which controls the coefficient memory 29, is connected to the memory 29. The blanking circuit 30 is also connected to the video switch 25 for circle blanking.

A weighting circuit 31, which may be set in any suitable manner, operates as an integrator or peak value detector, and is connected to the controllable amplifier 26. The weighting circuit 31 calculates either the mean value, the peak value, or the blank value of the output signal of the amplifier 26.

If the weighting circuit 31 is a peak value detector, an additional sampling is undertaken to determine whether this peak value is present with a defined area. Thus peak values which, for example, are produced by transirradiations having a small area are not acquired as a measured value. An area weighting of the BA signal of the video camera 6 is thus achieved.

A zero or null detector 32 is connected to the converter 28, and to a further input of the weighting circuit 31. The zero detector 32 disenables the weighting circuit 32 when the weighting factor is zero, i.e., when no weighting is to be undertaken.

The output signal from the weighting circuit 31 may be stored in a holding stage 33, to which the vertical pulses V of the video system are supplied as clock pulses. The output signal of the holding stage 33 forms the actual value S which, as described above, can be used to control the high voltage generator 1, the opening of the iris diaphragm 9, or the video amplifier in the video camera 6.

A coefficient memory 29 may be used to store a different weighting factor applicable to the entire area of the radiation image, with the entire signal, rather than only dominant regions thereof, contributes to the measurement. A modification of the weighting factors is undertaken by changing the coefficients in the memory 29, or by selecting a different set of coefficients via a control panel. The weighting factors, as in the digital embodiment, may be selected by an organ programmer. The remaining components of the digital embodiment shown in FIG. 2 can be used in combination with the analog circuitry shown in FIG. 3.

A location-dependent weighting of the overall image content is thus obtained, with a blanking of non-relevant image regions being achieved automatically, or by corresponding selection of programming keys. The calculation of the histogram permits a flexible, area-dependent weighting to be achieved which can automatically adapt to the subject under examination. The organ programming, or the weighting factors, can be appropriately automatically set based on the histogram as a result of the pattern recognition with the calculated histogram being compared to stored histogram allocated to the individual organs.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray diagnostics installation for examining a subject comprising:
- means for exposing an examination subject to an x-ray dose;
- means for generating an x-ray image from x-radiation attenuated by said subject;
- means for generating video signals comprising a video image from said x-ray image;
- a processing circuit, connected to said means for generating video signals, to which said video signals are directly supplied, including weighting means for assigning respectively different weighting factors to video signals corresponding to different regions of said video image to form weighted image regions, and means for combining said weighted image regions to form an actual value signal, said processing circuit connected to said means for exposing so as to supply said actual value signal thereto to control said x-ray dose; and
- said video image consisting of a plurality of picture elements, and said processing circuit further including data reduction means for combining respective portions of video signals corresponding to said plurality of picture elements to form said image regions, said data reduction means preceding said weighting means in said processing circuit.

2. An x-ray diagnostics installation as claimed in claim 1, wherein said means for generating video signals includes an iris diaphragm, wherein said installation further includes means for adjusting the opening of said iris diaphragm, and wherein said processing circuit is connected to said means for adjusting to supply said actual value signal additionally to said means for adjusting for controlling adjustment of said iris diaphragm.

3. An x-ray diagnostics installation for examining a subject comprising:
- means for exposing an examination subject to an x-ray dose;
- means for generating an x-ray image from x-radiation attenuated by said subject;
- means for generating video signals comprising a video image from said x-ray image;
- a processing circuit, connected to said means for generating video signals, to which said video signals are directly supplied, including weighting means for assigning respectively different weighting factors to video signals corresponding to different regions of said video image to form weighted image regions, and means for combining said weighted image regions to form an actual value signal, said processing circuit connected to said means for exposing so as to supply said actual value signal thereto to control said x-ray dose; and
- means for programming operating parameters for said installation corresponding to selected organs of said subject to be examined, said means for programming connected to said weighting means for selecting said weighting factors.

4. An x-ray diagnostics installation for examining a subject comprising:
- means for exposing an examination subject to an x-ray dose;
- means for generating an x-ray image from x-radiation attenuated by said subject;
- means for generating video signals comprising a video image from said x-ray image;
- a processing circuit, connected to said means for generating video signals, to which said video signals are directly supplied, including weighting means for assigning respectively different weighting factors to video signals corresponding to different regions of said video image to form weighted image regions, and means for combining said weighted image regions to form an actual value signal, said processing circuit connected to said means for exposing so as to supply said actual value signal thereto to control said x-ray dose; and
- means for generating histograms of said video image, said means for generating histograms connected to said weighting means for controlling selection of said weighting factors.

5. An x-ray diagnostics installation as claimed in claim 4 further comprising:
- detector means connected to said means for generating histograms for recognizing selected patterns in said video image.

6. An x-ray diagnostics installation for examining a subject comprising:
- means for exposing an examination subject to an x-ray dose;
- means for generating an x-ray image from x-radiation attenuated by said subject;
- means for generating video signals comprising a video image from said x-ray image;
- a processing circuit, connected to said means for generating video signals, to which said video signals are directly supplied, including weighting means for assigning respectively different weighting factors to video signals corresponding to different regions of said video image to form weighted image regions, and means for combining said weighted image regions to form an actual value signal, said processing circuit connected to said means for exposing so as to supply said actual value signal thereto to control said x-ray dose; and
- said means for generating video signals including a video camera with a controlled-gain video amplifier, and said processing circuit being connected to a control input of said controlled-gain video amplifier to supply said actual value signal thereto for controlling the gain of said amplifier.

* * * * *